(12) United States Patent
Chesnin et al.

(10) Patent No.: US 8,414,545 B2
(45) Date of Patent: *Apr. 9, 2013

(54) GUARD FOR FLEXIBLE TUBING CLAMP AND METHOD OF USING SAME

(75) Inventors: Kenneth J. Chesnin, Philadelphia, PA (US); John Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/241,535

(22) Filed: Sep. 23, 2011

(65) Prior Publication Data

US 2012/0016317 A1 Jan. 19, 2012

Related U.S. Application Data

(63) Continuation of application No. 12/122,965, filed on May 19, 2008, now Pat. No. 8,025, 645.

(60) Provisional application No. 60/931,917, filed on May 25, 2007.

(51) Int. Cl.
*A61M 5/00* (2006.01)
*A61M 1/00* (2006.01)

(52) U.S. Cl.
USPC ............... 604/250; 604/34; 604/246

(58) Field of Classification Search .................... 604/30, 604/34, 246, 250; 251/10; 137/382; 239/288; 138/110
See application file for complete search history.

(56) References Cited

U.S. PATENT DOCUMENTS

| | | |
|---|---|---|
| 4,097,020 A | 6/1978 | Sussman |
| 4,235,412 A | 11/1980 | Rath et al. |
| 4,453,295 A | 6/1984 | Laszczower |
| 4,497,124 A | 2/1985 | Olive |
| 4,876,810 A | 10/1989 | Piana et al. |
| 5,035,399 A | 7/1991 | Rantanen-Lee |
| 5,203,056 A | 4/1993 | Funk et al. |
| 5,300,044 A | 4/1994 | Classey et al. |
| 6,089,527 A | 7/2000 | Utterberg |
| 6,823,617 B2 | 11/2004 | Schweikert |
| 6,942,647 B2 | 9/2005 | Nickels |
| 8,025,645 B2 * | 9/2011 | Chesnin et al. ............. 604/250 |
| 2008/0051731 A1 * | 2/2008 | Schweikert et al. ......... 604/250 |

* cited by examiner

*Primary Examiner* — Bhisma Mehta
(74) *Attorney, Agent, or Firm* — Glenn M. Massina, Esq.; Fox Rothschild LLP

(57) ABSTRACT

A clamp guard for securing to flexible tubing such as catheters and their extension tubes and about a clamp therealong for housing the clamp at least when the clamp is in a tubing-clamping state, to prevent inadvertent contact of the clamp by a foreign body and undesirable unclamping of the clamp. The clamp guard is removable from around the clamp when desired.

14 Claims, 9 Drawing Sheets

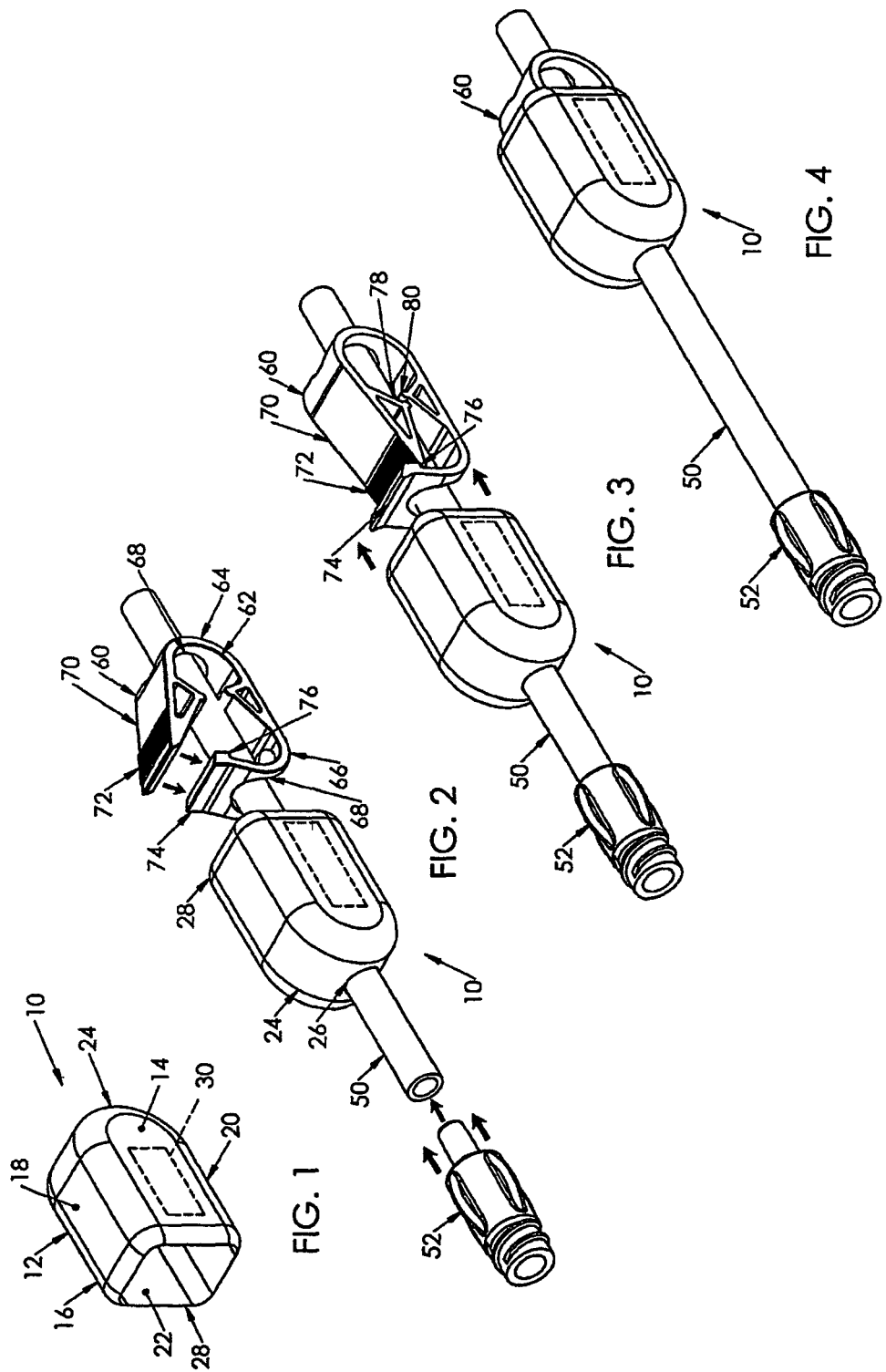

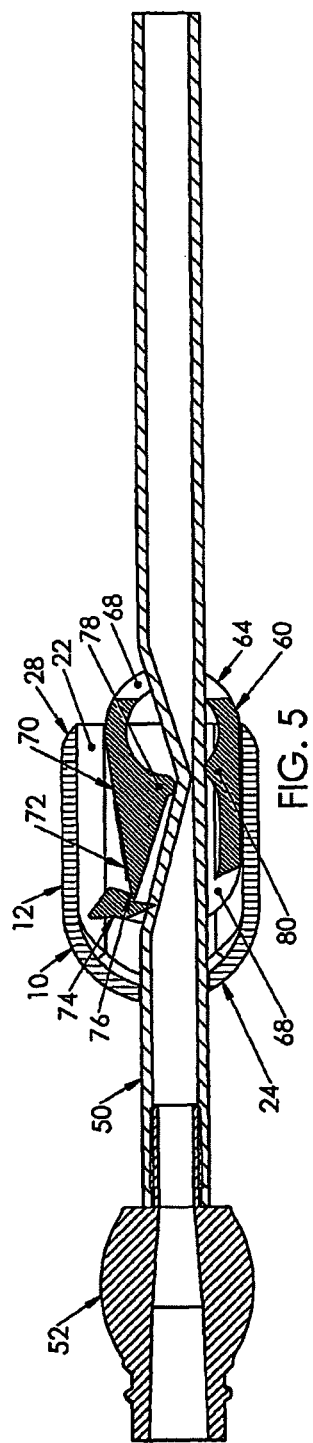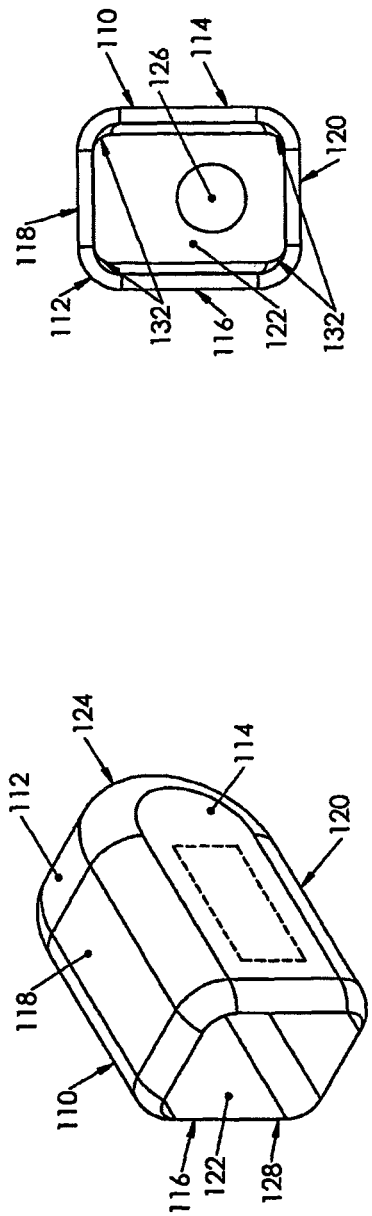

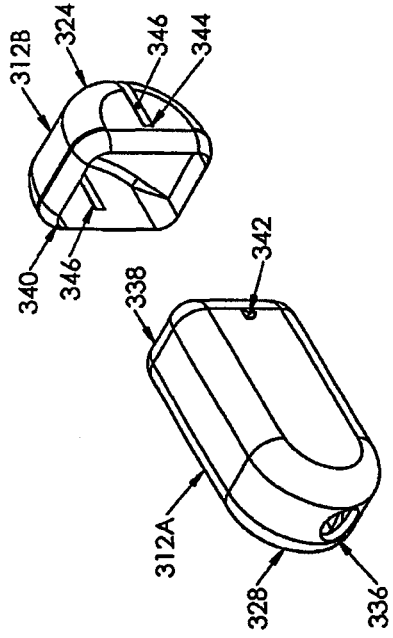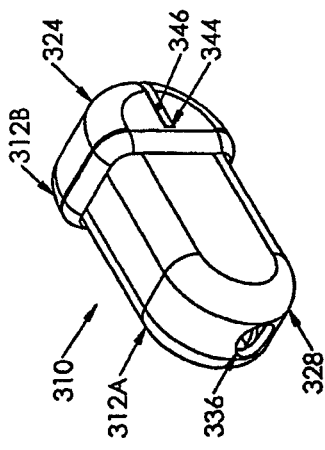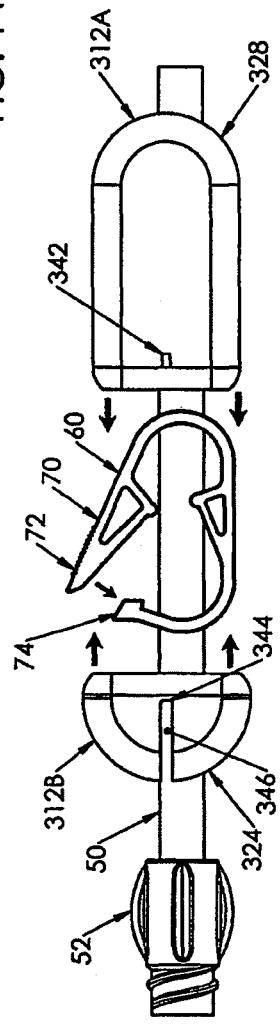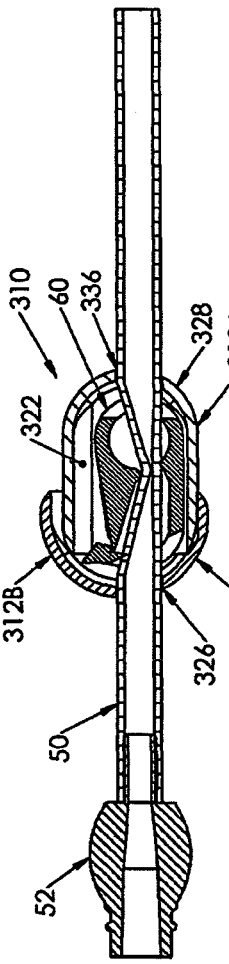

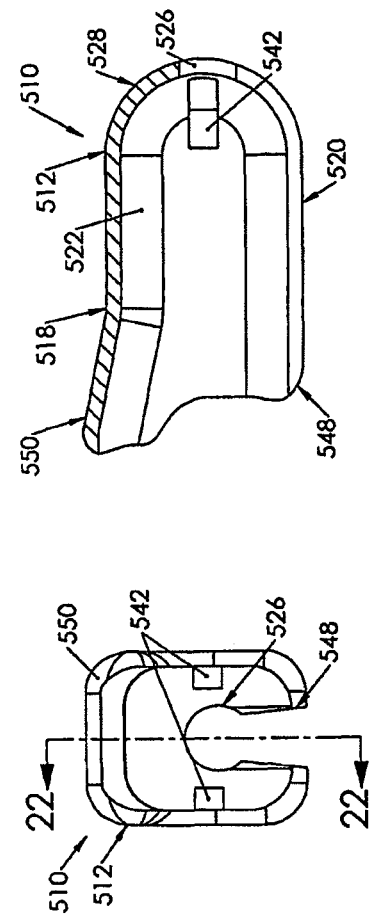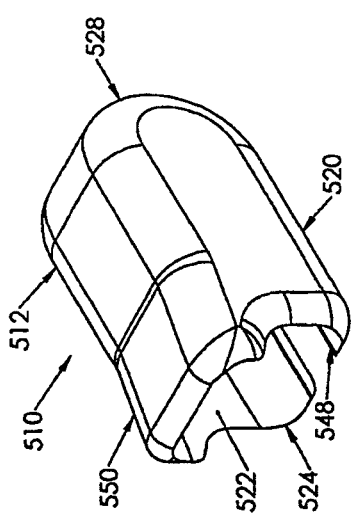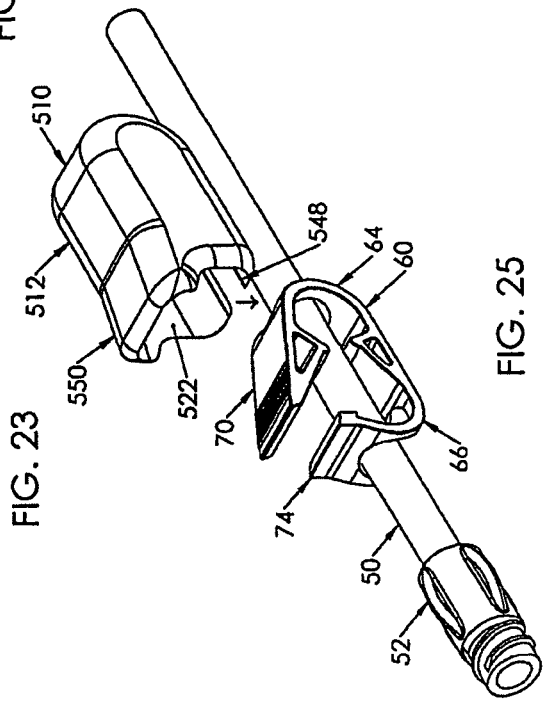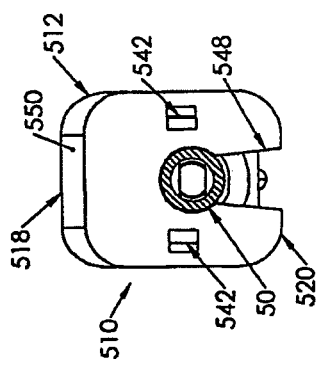

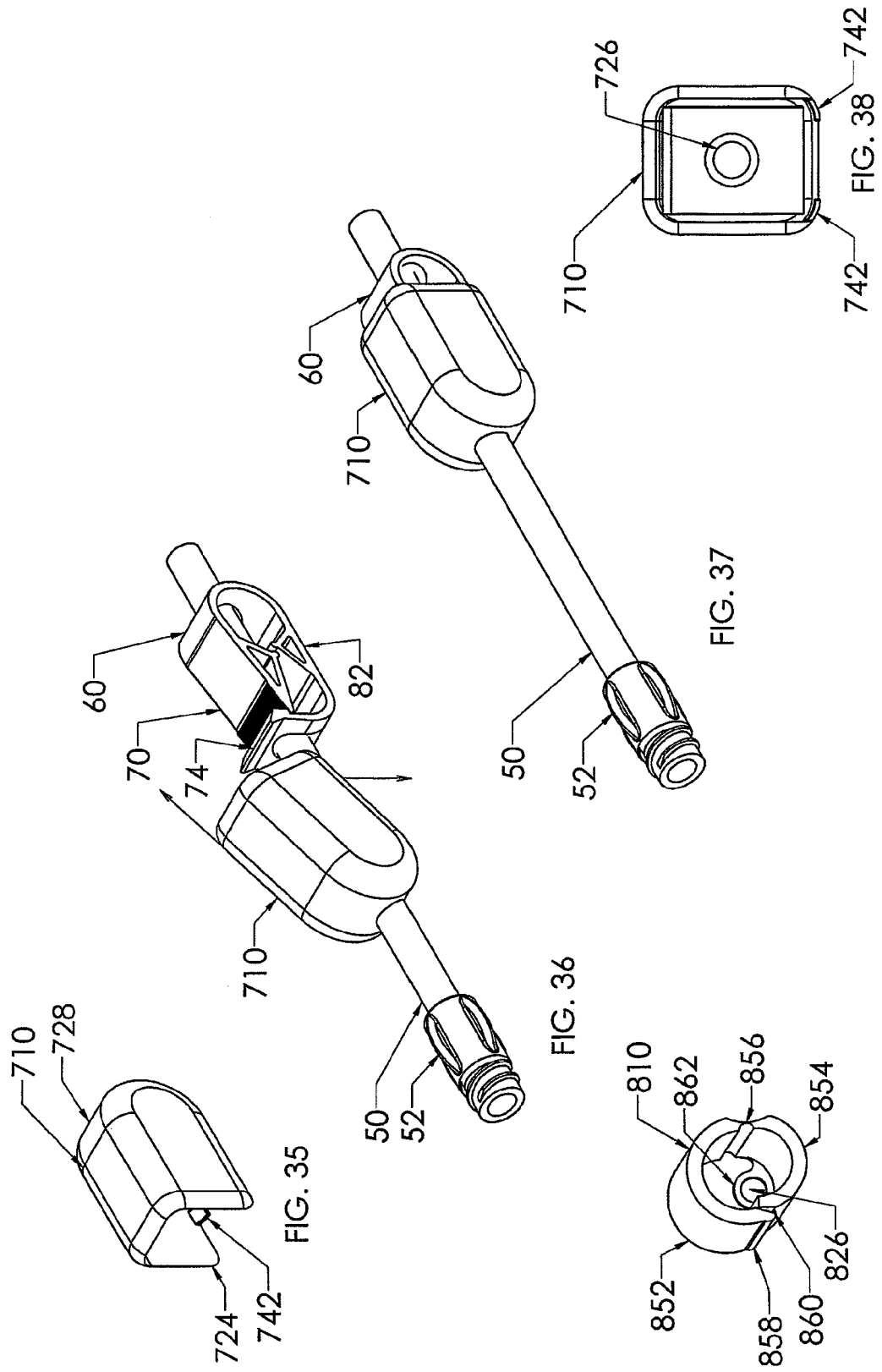

US 8,414,545 B2

GUARD FOR FLEXIBLE TUBING CLAMP AND METHOD OF USING SAME

CROSS-REFERENCE TO RELATED APPLICATIONS

This application is a continuation application of U.S. application Ser. No. 12/122,965 filed May 19, 2008, now U.S. Pat. No. 8,025,645, which claims the benefit of U.S. Provisional Patent Application Ser. No. 60/931,917 filed May 25, 2007.

FIELD OF THE INVENTION

This relates to flexible tubing and more particularly to medical tubing such as catheters and their extension tubes and to clamp devices therefor.

BACKGROUND OF THE INVENTION

Catheters for the introduction or removal of fluids may be located in various venous locations and cavities throughout the body for the introduction or removal of such fluids. Such catheterization may be performed by using a single catheter having multiple lumens. A typical example of a multiple lumen catheter is a dual lumen catheter in which a first lumen introduces fluids and a second lumen removes fluids. These catheters are very useful for procedures such as hemodialysis, wherein blood is removed from a patient through the first lumen for processing in a hemodialysis machine, and the processed blood is returned to the patient through the second lumen. Alternatively, multiple catheters, each having a single lumen, may be inserted in multiple locations in the patient, such as in each femoral vein.

Many such catheter assemblies are presently utilized that include extension tube assemblies at proximal ends of the lumens of multi-lumen catheters, and clamps are commonly used that allow manual actuation to clamp and unclamp the extension tubes to occlude fluid flow therethrough at selected times, such as during connection to and disconnection from tubing of hemodialysis machines. One particularly popular clamp is an in-line pinch clamp known as a Halkey-style or Roberts clamp, which has: a skeletal-like framework 62 defining an axially extending body portion having transverse distal and proximal end portions 64, 66; tube openings 68 through its transverse distal and proximal end portions 64, 66 through which the tubing 50 extends; a flexible latching arm 70 extending proximally from the distal end portion 64 thereof to a free end 72, and the transverse proximal end portion 66 of the clamp comprising a catch arm 74 extending to a free end upon which is defined a catch 76, for the latch arm free end 72 to become latched thereto; and cooperating clamping sections 78, 80 that impinge on the tubing 50 to occlude it when the clamp 60 is in its clamping state, one clamping section 78 being on the flexible arm 70 and the other being defined on the axially extending body portion, both intermediate the distal and proximal ends 64, 66. The latching arm 70 is adapted to be easily manipulated by hand between latching and unlatching conditions that correspond with clamping and unclamping states of the clamp 60. Such a clamp 60 would be maintained in the clamped state most of the time, that corresponds to all times other than when a practitioner is performing hemodialysis or infusion, or is withdrawing a blood sample.

Such a clamp in its latched and clamped state has a drawback in that the free end of the catch arm can snag on clothing, linens, tubing, wiring and other articles and snag and strain the tubing and the catheter, potentially harming the patient or damaging the catheter assembly. Even more problematic is that the catch arm free end can snag sufficiently to unlatch the latching arm resulting in unclamping of the clamp permitting blood to flow freely from the patient, causing great harm, especially when the patient is unattended in order for remedial action to be performed.

It is desired to provide a way of minimizing the possibility of the tubing clamp snagging or becoming inadvertently unclamped.

BRIEF SUMMARY OF THE INVENTION

The present invention is directed to an article for placement about a flexible tubing clamp to guard against accidental opening thereof when in its clamped state occluding fluid flow through the flexible tubing. Preferably, the article envelopes most of the clamp to minimize any snagging by any portion of the clamp and also itself possesses a snagging-free external surface, such as by having minimal if any protrusions, and also, preferably, having rounded exposed edges and corners, which also presents an additional advantage of patient comfort.

In one embodiment, the article is a housing that is adapted to be placed along the tubing adjacent to the clamp and that has distal and proximal openings in its distal and proximal ends, with the distal opening of the housing defining a large clamp-receiving opening and being adjacent the proximal end of the clamp, while the proximal opening is sufficiently large for the tubing to pass therethrough. The housing would preferably be movable along the tubing to envelop the clamp at least when the clamp is in its clamping state at which time the flexible latch arm of the clamp is in its latched state and such that the end of the clamp at which the free end of the latching arm is disposed, is totally within the housing.

In another embodiment, the guard is a housing similar to that described above, wherein the interior of the housing is so dimensioned as to define a friction fit with the clamp wherein the housing is maintained about the clamp.

In a third embodiment, similar to those described hereinabove, the guard housing includes an opening at its relatively closed end so shaped and dimensioned for receipt thereinto of the free end of the catch of the clamp in a snap-fit, for holding the guard housing in position about the clamp.

In a fourth embodiment, the guard is a housing similar to those described hereinabove, wherein the housing is a two-part housing, the housing parts disposed about and along the flexible conduit in respective positions distally and proximally from the distal and proximal ends of the clamp, wherein the two housing parts are adapted to be secured together about the clamp.

Additional embodiments of the guard of the present invention are disclosed wherein the guard housing is positioned along the flexible conduit distally of the clamp and are translatable along the conduit to envelop the clamp from the distal end thereof, that is, the end from which the latching arm of the clamp extends. In a fifth embodiment, the guard housing defines an interior that is large enough just to receive the distal end portion of the clamp thereinto when the latching arm is in its latched state, and would define a friction fit with the clamp. While the free end of the proximal end portion of the clamp (i.e., the catch arm) would protrude from the housing and thus be exposed, the latching arm would be secured in its latched state by abutment with the guard housing even if the catch arm became inadvertently snagged.

In a sixth embodiment, similar to the fifth, the guard housing defines an interior that, at the housing end remote from the clamp-receiving opening, includes a diverging top wall of the clamp-receiving opening that creates an enlarged interior clearance area that can receive thereinto the free end of the catch arm of the clamp that would obviate any snagging of the catch arm.

A seventh embodiment of guard housing is similar to the immediately preceding embodiment, except that the end portion of the top wall does not diverge but instead protrudes beyond the proximal end of the housing and includes an overhang that defines a snap-fit with the free end of the catch arm to assure securing of the guard housing about the clamp when the clamp is fully received into the housing.

Further, the embodiments could be adapted for retrofit application by including a clip structure for being applied laterally to the length of tubing, and could also have internal latch projections to latch to the clamp's skeletal-like framework.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is an isometric view of a first embodiment of clamp guard of the present invention;

FIGS. 2 to 4 are isometric views of the clamp guard of FIG. 1 disposed along an extension tube between a fitting and a clamp, respectively, spaced apart with the clamp in an opened state and the fitting being applied (FIG. 2); spaced apart with the clamp in a closed clamping state (FIG. 3); and the guard enveloping the clamp in its closed clamping state (FIG. 4);

FIG. 5 is a longitudinal cross-section view of the clamp guard assembled to the clamp as in FIG. 4;

FIGS. 6 and 7 are an isometric and distal end view a second embodiment of clamp guard;

FIGS. 13 and 14 are an isometric views of a fourth embodiment of clamp guard having two parts that are assembled together about a clamp;

FIGS. 15 and 16 are elevation and cross-section views of the clamp guard of FIGS. 13 and 14 assembled to an extension tube spaced apart from and assembled about the clamp, respectively;

FIG. 21 is an isometric view of a sixth embodiment of clamp guard of the present invention adapted to be assembled to an extension tube from laterally thereof, and having internal latches to latch to the clamp;

FIGS. 22 to 24 are cross-sectional, proximal and distal views of the clamp guard of FIG. 21, with FIG. 24 shown assembled to an extension tube and enveloping the clamp;

FIGS. 25 to 29 are elevation and cross-section views of an extension tube with a fitting and a clamp, and the clamp guard of FIGS. 21 to 24, showing, respectively, the clamp guard being assembled to the tubing, on the tubing with the clamp open, with the clamp closed, and with FIGS. 28 and 29 enveloping the clamp in elevation and cross-section views, respectively;

FIGS. 35 to 38 are views of an eighth embodiment of clamp guard of the present invention; and FIG. 39 is an isometric view of a ninth embodiment of clamp guard having a hinge.

DETAILED DESCRIPTION OF THE INVENTION

Figure 10:
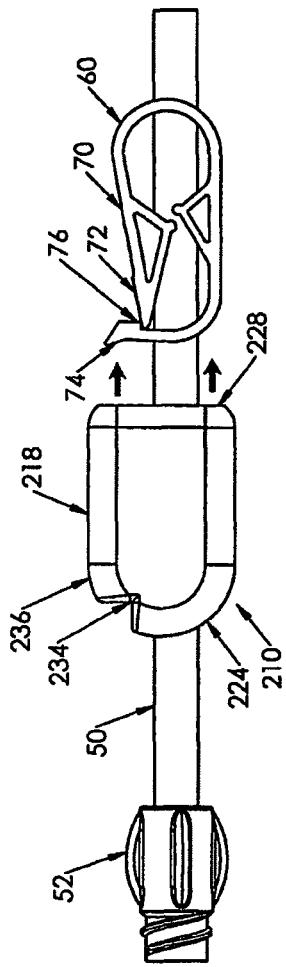
FIGS. 10 to 12 are elevation views and a cross-section view similar to FIGS. 3 to 5 of the clamp guard of FIGS. 8 and 9.

In the drawings, like numerals indicate like elements throughout. Certain terminology is used herein for convenience only and is not to be taken as a limitation on the present invention. Flexible tubing or conduit includes catheters and extension tubes therefore, without limitation. The terms "distal" and "proximal" refer, respectively, to directions away from and closer to the latching arrangement of the clamp. "Tubing" refers to flexible tubing of the type used in medical devices and includes catheters, intravenous tubing and extension tubes of catheters assemblies. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Generally, clamp members illustrated herein are of the Roberts type, but the present invention is not restricted to only this type of clamp; modifications may be made to the indicia-bearing article of the present invention to adapt to different styles of clamps, within the skill of the artisan.

In the first embodiment shown in FIGS. 1 to 5, a first embodiment of clamp guard device 10 includes a body 12 having a pair of side walls 14,16, a top wall 18, bottom wall 20, an interior 22 and a proximal or first end 24 having a first end wall with a tube aperture 26, and an open distal or second end 28. The clamp guard thus defines an opening extending between the first and second ends, the opening being dimensioned to permit sliding of the clamp guard along the tubing. The clamp guard may be placed onto the tubing adjacent the proximal clamp end, as shown in FIGS. 1 to 5. Optionally, one or more walls of the clamp guard 10 may have indicia thereon, as indicated at 30. Also seen in FIGS. 2 to 5 is an assembly of a length of flexible tubing 50, a fitting 52 affixed to a proximal end of the tubing, and a clamp member 60 secured along the tubing 50, the clamp being manipulatable between an unclamping state, permitting fluid flow through the tubing into (or from) the patient when desired, and a clamping state in which fluid flow through the tubing 50 is occluded thereby preventing the flow of blood from the patient.

Generally, with respect to all of the disclosed embodiments, the clamp guard devices may be made of soft pliable polyurethane like 80A PELLETHANE® polymer (a product of Dow Chemical Co.), or silicone elastomer, or may be made of ABS, polyvinyl chloride, polypropylene or other suitable plastic materials that may alternatively produce semi-rigid or rigid properties. The clamp members may be made of similar suitable plastic materials but have substantial rigidity to maintain clamping of the flexible tubing; in-line pinching clamps are commonly made of polypropylene or acetal. The flexible tubing may be biocompatible elastomers such as silicone rubber, usually for catheters, or polyurethane, usually for extension tubing or some catheters.

Further, with respect to all embodiments, it is preferred that the exposed edges of the guard be gently rounded to minimize skin irritation of the patient, problematic especially in certain patient populations with compromised skin such as patients with diabetes. Generally speaking, the guard of the present invention would fit snuggly about the clamp, or remain in position therearound such as by latches or snap fit, protect against inadvertent and undesirably unclamping of the clamp from the tubing, and be removable therefrom when it is desired to unclamp the clamp from the tubing.

FIGS. 6 and 7 show a second embodiment of clamp guard 110 with a pair of side walls 114, 116, top and bottom walls 118, 120, a proximal end 124 with tube aperture 126, and a distal end 128. In this embodiment, guard body 112 is narrower between side walls 114, 116, enabling proximal end 124 to establish a friction fit at internal corners 132 or along interior side surfaces with upper and lower side edges of a tubing clamp such as clamp 60 of FIGS. 2 to 5, upon receipt thereof into guard interior 122 when the clamp is in its closed state as in FIG. 5. Clamp guard 110 is removable from about clamp 60 permitting access thereto for unclamping the tubing, when desired.

Figure 11:
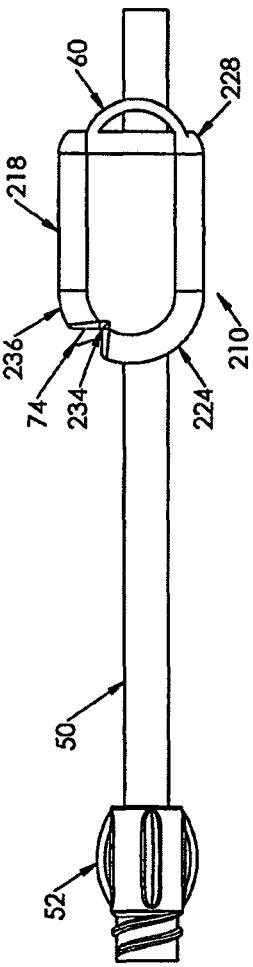
Figure 12:
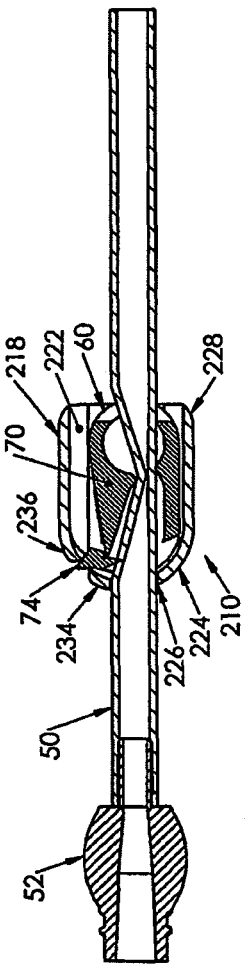
Figure 8:
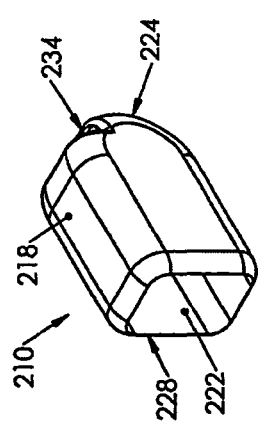
FIGS. 8 and 9 are an isometric and distal end view a third embodiment of clamp guard.
Figure 9:
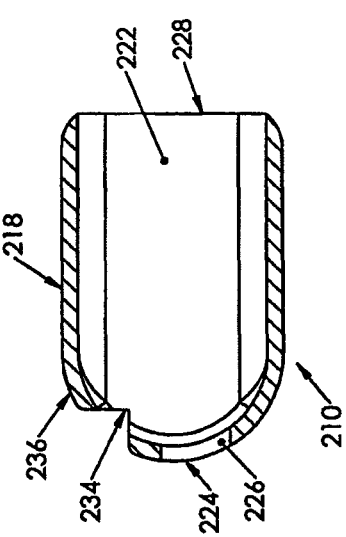
Figure 17:
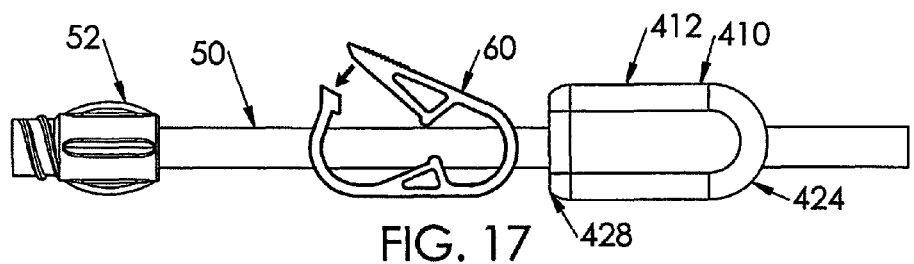
FIGS. 17 to 20 are elevation views and a cross-section view of a fifth embodiment of clamp guard assembled along an extension tube similar to FIGS. 2 to 5, with the clamp guard similar to that of FIG. 1.
Figure 18:
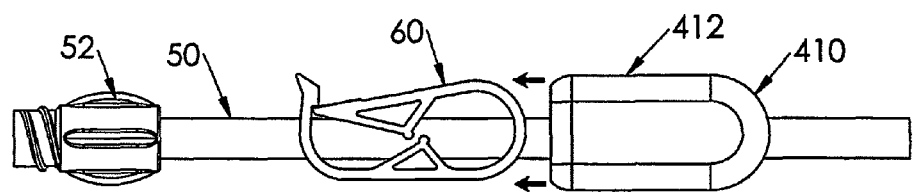
Figure 19:
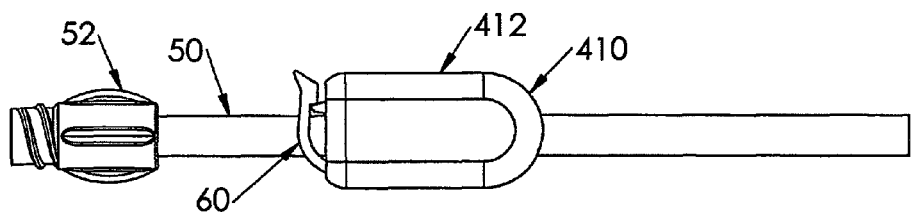
Figure 20:
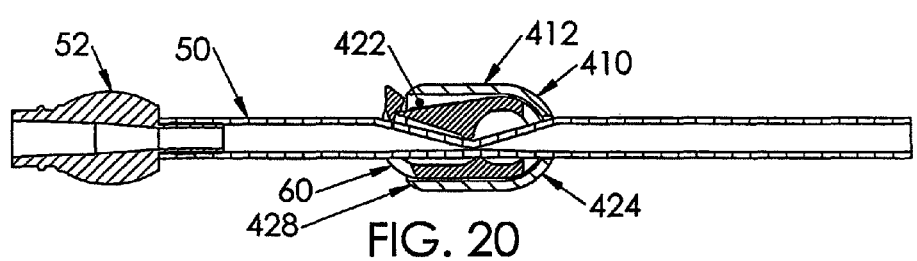
Figure 26:
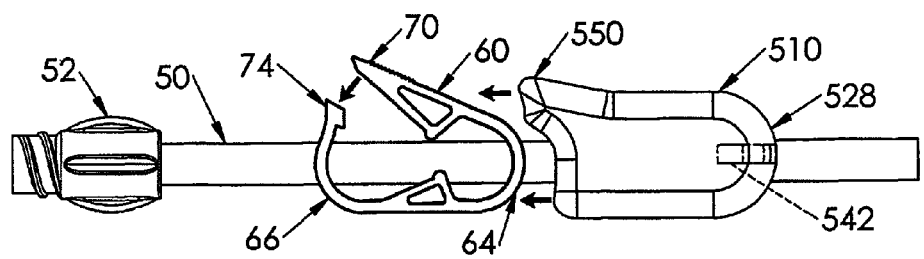
Figure 27:
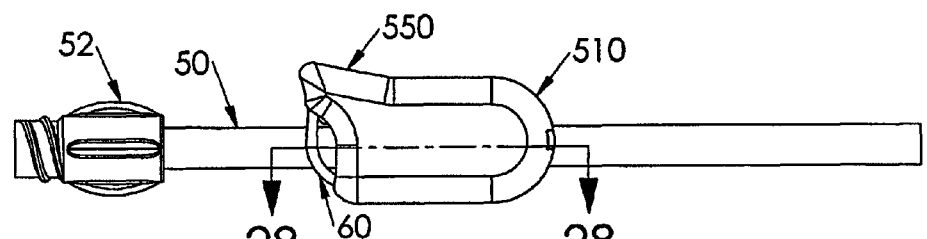
Figure 28:
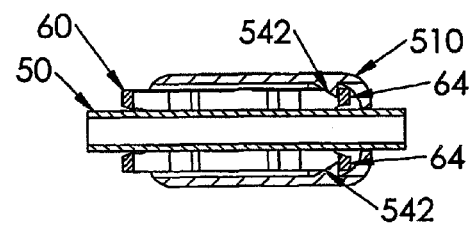
Figure 29:
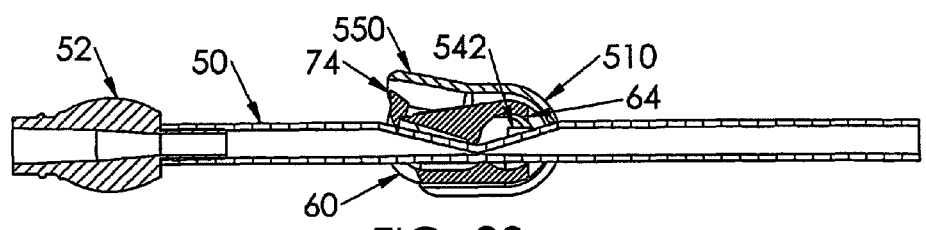
Figures 30, 31:
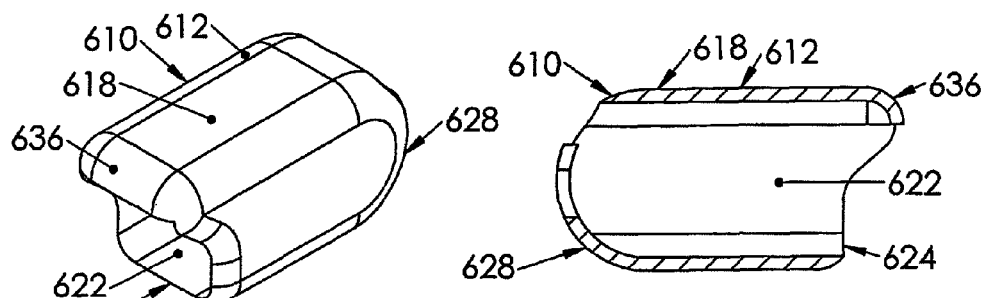
FIGS. 30 to 34 are views of a seventh embodiment of clamp guard of the present invention.
Figure 32:
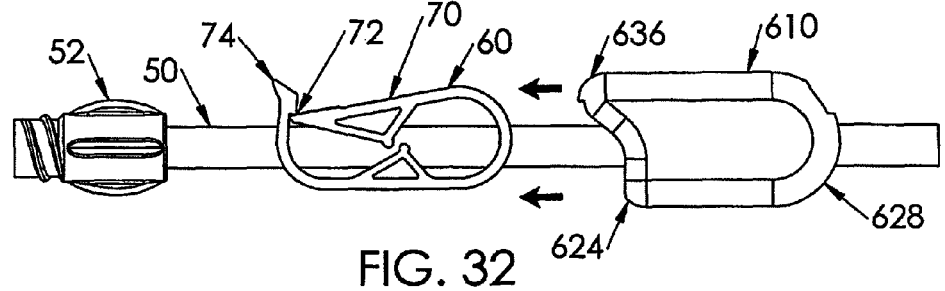
Figure 33:
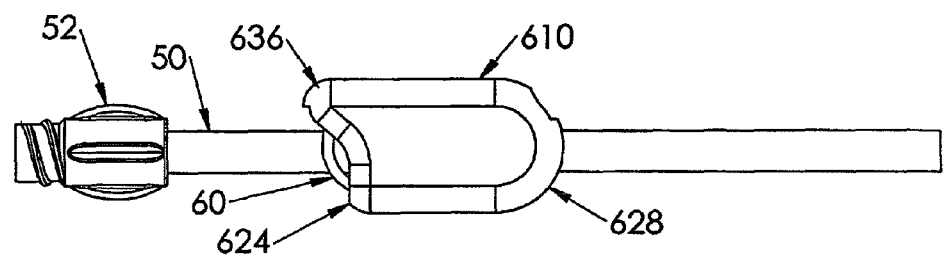
Figure 34:
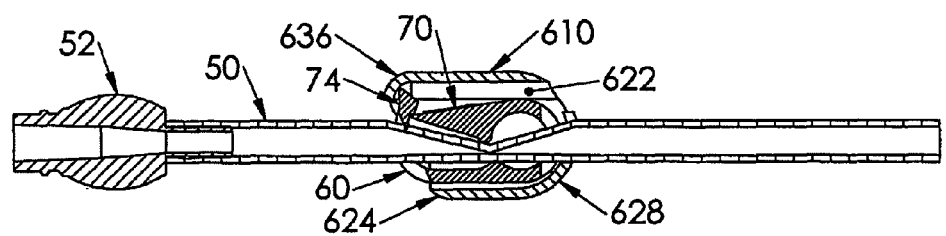

Clamp guard 210 of FIGS. 8 to 12 provides for a latching arrangement to secure the clamp guard about the clamp 60 in its clamping state along the flexible tubing 50. Clamp guard 210 has a distal or second end 228 open for receipt into its interior 222 of the clamp as the proximal or first end 224 includes an opening 226 through which extends the tubing 50. Clamp guard 210, and clamp guards 10 and 110, have imperforate clamp-surrounding top, bottom and side walls in a generally rectangular cross-section. A transverse opening 234 is defined at the clamp guard's first end wall at the junction of top wall 218 and proximal end 224, associated with catch arm 74 of clamp 60, which is at the first end of the clamp. As seen in FIGS. 11 and 12, when clamp 60 is in its clamping state and latch arm 70 is latched to catch arm 74, clamp guard 210 is moved along tubing 50 until clamp 60 is received into interior 222; catch arm 74 snaps into transverse opening 234 and latches behind, or proximally of, overhang 236 of top wall 218 of the clamp guard, holding the clamp guard in position about the clamped clamp in a manner permitting removal therefrom for unclamping from the tubing, when desired.

In FIGS. 13 to 16, clamp guard embodiment 310 is seen to comprise two housing parts, 312A and 312B, that self-secure to each other about the clamped clamp 60 in a manner permitting disassembly to access the clamp for unclamping when desired. Housing parts 312A and 312B each have a transverse end section 324,328 respectively each having an opening 336,326 through which the tubing extends, and each has an open opposite end 338,340 enabling receipt thereinto of ends of the clamp. Housing part 312A defines an interior cavity 322 which receives a larger portion of the clamp 60. Preferably, housing part 312A is disposed distally of the clamp along the tubing 50, and housing part 312B is disposed proximally of the clamp, as seen in FIGS. 15 and 16, and both housing parts are translatable along the tubing and about the clamp after which the housing parts latch to each other. As shown, the distal end 338 of housing part 312A is received into proximal end 340 of housing part 312B, and latch projections 342 at the distal end of housing part 312A latch into ends 344 of latch slots 346 along side walls of housing part 312B for latching the housing parts to each other about the clamp 60.

Another embodiment of clamp guard 410 is seen in FIGS. 17 to 20, comprising a unitary housing 412 having a distal or first end 424 and a proximal or second end 428. Clamp guard 410 is disposed along the tubing distally of the clamp and is translatable proximally to receive all but the proximal end of the clamp 60 into interior 422 thereof. Clamp guard 410 is dimensioned to establish a friction fit with and about clamp 60 when in its clamping state, in a manner permitting removal therefrom for accessing the clamp for unclamping the tubing.

Clamp guard embodiment 510 of FIGS. 21 to 29 also comprises a unitary housing 512. Clamp guard 510 is similar to clamp guard 410 of FIGS. 17 to 20 except that it is adapted to latch directly onto the clamp. Clamp guard 510 is seen to provide a wide slot 548 along a longitudinally extending wall such as bottom wall 520 and continuing along distal or first end section 528 and opening onto distal opening 526, but having a width dimension less than the diameter of the tubing facilitating clamp guard self-retention onto the tubing; slot 548 opens to the interior and permits clamp guard 510 to be secured onto the flexible tubing from laterally thereof, as seen in FIGS. 24 and 25. Within interior 522 of clamp guard 510, adjacent to distal end section 528 thereof, are a pair of integral opposed latch projections 542 on inside surfaces of opposed sidewalls that are shaped and dimensioned to latch proximally of the proximal inside surface of clamp distal end 64, as seen best in FIG. 28. (In FIG. 24, latch projections 542 are seen because of apertures through distal end section 528 remaining as relics from the molding process.) At the proximal or second end 524 of clamp guard 510, the top wall 518 includes an outwardly angled wall portion 550 that will be disposed outwardly of and over catch arm 74 of clamp 60, as an overhang, to inhibit snagging thereof by any foreign objects such as tubing, wires, clothing and so on that could otherwise tend to inadvertently and undesirably unclamp the clamp from the tubing.

An additional clamp guard embodiment 610 is illustrated in FIGS. 30 to 34, comprising a unitary housing 612 extending between a proximal end 624 and a distal end 628 with an interior cavity 622. This embodiment is similar to clamp guard 210 of FIGS. 8 to 12, but is disposed on tubing 50 distally of clamp 60. Top wall 618 of housing 612 includes an overhang 636 at otherwise open proximal end 624 that will snap over catch arm 74 of clamp 60.

A further, eighth embodiment of clamp guard 710 is shown in FIGS. 35 to 38, wherein the clamp guard distal end 724 includes a tubing opening 726 through the proximal wall 728, similar to the clamp guards of FIGS. 2 and 7; optionally, a slotted entrance could be provided similar to that in the clamp guard configuration of FIG. 22. Further, the embodiment lacks a bottom wall, so that it may be clipped onto the tubing and moved adjacent the proximal end of the clamp and then rotated or pivoted about the clamp in its closed position. A pair of catches 742 facing each other at the bottom edges of the opposing clamp guard sidewalls, will latch onto and about the bottom edges 82 of the clamp to secure the clamp guard in position about the clamp.

In FIG. 39, a ninth embodiment of clamp guard 810 is illustrated. Clamp guard 810 has two half portions 852,854 joined to each other by a living hinge 856. A first half portion 852 includes a latch member 858 along the opposite side from the hinge, and the second half portion 854 includes a catch 860 along the opposite side from the hinge. The first and second half portions can be pivoted about living hinge 856 until latch member 858 and catch 860 latchingly engage, for clamp guard 810 to be secured about a clamp. A transverse body section 862 may be included at one end of clamp guard 810, having a tubing aperture 826 therethrough by which the clamp guard can be secured to the tubing during assembly.

Further variants of the invention include a guard of two parts latchable to each other directly around the clamp in similar fashion to the clamp guard of FIGS. 35 to 38, without self-retaining to the flexible tubing directly (not shown). It is also foreseeable that the clamp guard of the present invention may be free of one of the two side walls, or be free of a bottom wall or a distal end wall.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the appended claims.

What is claimed is:

1. A guard for use with a tubing assembly, the tubing assembly having a length of flexible tubing and a tubing clamp disposed therealong and therearound, the tubing clamp including a latch arm and a clamp arm which are moveable relative to one another between two states, an unclamping state and a tubing-clamping state wherein the flexible tubing is occluded, the guard comprising:
a housing body extending between first and second ends with an interior cavity extending between the ends, the first end defining a first opening in communication with the interior cavity and configured for passage of the flexible tubing therethrough such that the housing body is moveable along the tubing, and the second end defining a second opening in communication with the interior cavity, the second opening being larger than the first opening and configured such that the housing body is movable along the tubing from a first position relative to the tubing clamp toward a second position relative to the tubing clamp wherein the tubing clamp passes into the interior cavity when the latch arm and clamp arm are in the tube-clamping state, wherein in the second position the housing body is configured to encompass the tubing clamp and prevent relative movement between the latch arm and the clamp arm.

2. The guard of claim 1, wherein the housing body is of unitary construction.

3. The guard of claim 1, wherein the housing body includes opposed portions hingedly connected to one another.

4. The guard of claim 1, wherein a longitudinal slot extends along the housing body between the first and second ends and is in communication with the interior cavity, wherein at least a portion of the slot has a width less than an outer diameter of the tubing.

5. The guard of claim 1, wherein at least one wall portion of the housing body includes indicia on an exterior surface thereof.

6. The guard of claim 1, wherein the housing body is configured to receive the tubing clamp with a snug fit.

7. The guard of claim 1, wherein the housing body includes internally projecting latches configured to engage the tubing clamp to secure the housing body to the clamp.

8. The guard of claim 7, wherein the latches are disposed along inside surfaces of opposed side walls of the housing body adjacent the first end thereof.

9. The guard of claim 1, wherein the housing body defines an overhang in the first end wall which is configured to latchably engage the latch arm.

10. The guard of claim 1, wherein the housing body includes a top wall having an outwardly angled wall section at its second end to extend over the latch arm.

11. A combination of a tubing clamp and a guard, for use with flexible tubing, wherein:
the tubing clamp includes a latch arm and a clamp arm which are moveable relative to one another between two states, an unclamping state and a tubing-clamping state wherein the flexible tubing is occluded; and
the guard including a housing body extending between first and second ends with an interior cavity extending between the ends, the first end defining a first opening in communication with the interior cavity and configured for passage of the flexible tubing therethrough such that the housing body is moveable along the tubing, and the second end defining a second opening in communication with the interior cavity, the second opening being larger than the first opening and configured such that the housing body is movable along the tubing from a first position relative to the tubing clamp toward a second position relative to the tubing clamp wherein the tubing clamp passes into the interior cavity when the latch arm and clamp arm are in the tube-clamping state, wherein in the second position the housing body is configured to encompass the tubing clamp and prevent relative movement between the latch arm and the clamp arm.

12. A tubing assembly comprising:
a length of flexible tubing having a first end and a second end, wherein the tubing further comprises a fitting fixedly connected to the first end of the tubing;
a tubing clamp disposed along and around the tubing, the tubing clamp including a latch arm and a clamp arm which are moveable relative to one another between two states, an unclamping state and a tubing-clamping state wherein the flexible tubing is occluded; and
a guard including a housing body extending between first and second ends with an interior cavity extending between the ends, the first end defining a first opening in communication with the interior cavity and configured for passage of the flexible tubing therethrough such that the housing body is moveable along the tubing, and the second end defining a second opening in communication with the interior cavity, the second opening being larger than the first opening and configured such that the housing body is movable along the tubing from a first position relative to the tubing clamp toward a second position relative to the tubing clamp wherein the tubing clamp passes into the interior cavity when the latch arm and clamp arm are in the tube-clamping state, wherein the housing body is configured to encompass the tubing clamp and prevent relative movement between the latch arm and the clamp arm.

13. A method of protecting a tubing clamp for clamping flexible tubing, comprising the steps of:
clamping a tubing clamp positioned along a length of the flexible tubing into a tubing clamping state by moving a latch arm and a clamp arm relative to one another; and
manipulating a guard, including a housing body extending between first and second ends with an interior cavity extending between the ends, along the tubing with the tubing passing through a first opening in the housing first end which is in communication with the interior cavity until the tubing clamp is received through a second opening in the second end of the housing body and into the interior cavity, such that the housing body encompasses the tubing clamp and prevents relative movement between the latch arm and the clamp arm.

14. The method of claim 13, comprising the further steps of removing the housing body from around the tubing clamp and unclamping the clamp from the tubing.

* * * * *